(12) United States Patent
Hamilton

(10) Patent No.: US 11,358,966 B2
(45) Date of Patent: Jun. 14, 2022

(54) PYRIDINE OR N,N-DIMETHYL ACETAMIDE SOLVATED SOLID STATE FORMS OF SOLVATED IDELALISIB, THEIR USE AND PREPARATION

(71) Applicant: Johnson Matthey Public Limited Company, London (GB)

(72) Inventor: Clifton R. Hamilton, Devens, MA (US)

(73) Assignee: Johnson Matthey Public Limited Company, London (GB)

( * ) Notice: Subject to any disclaimer, the term of this patent is extended or adjusted under 35 U.S.C. 154(b) by 0 days.

(21) Appl. No.: 16/948,361

(22) Filed: Sep. 15, 2020

(65) Prior Publication Data

US 2021/0017181 A1 Jan. 21, 2021

Related U.S. Application Data

(63) Continuation of application No. PCT/US2019/022757, filed on Mar. 18, 2019.

(60) Provisional application No. 62/644,062, filed on Mar. 16, 2018.

(51) Int. Cl.
*C07D 473/34* (2006.01)
*A61K 31/52* (2006.01)
*A61P 35/00* (2006.01)

(52) U.S. Cl.
CPC ........ *C07D 473/34* (2013.01); *C07B 2200/13* (2013.01)

(58) Field of Classification Search
CPC .. C07D 473/34; C07B 2200/13; A61K 31/52; A61P 35/00
See application file for complete search history.

(56) References Cited

U.S. PATENT DOCUMENTS

| | | | |
|---|---|---|---|
| 6,800,620 B2 | 10/2004 | Sadhu et al. | |
| 6,949,535 B2 | 9/2005 | Sadhu et al. | |
| 8,138,195 B2 | 3/2012 | Sadhu et al. | |
| 8,492,389 B2 | 7/2013 | Sadhu et al. | |
| RE44,638 E | 12/2013 | Fowler et al. | |
| 8,637,533 B2 | 1/2014 | Sadhu et al. | |
| 8,865,730 B2 | 10/2014 | Carra et al. | |
| 9,469,643 B2 | 10/2016 | Carra et al. | |
| 9,518,059 B2 | 12/2016 | Zhang et al. | |
| 9,567,337 B2 | 2/2017 | Bremner et al. | |
| 9,708,327 B2 | 7/2017 | Buttar et al. | |
| 10,370,376 B2 | 8/2019 | Zhang et al. | |
| 10,414,737 B2 | 9/2019 | Bremner et al. | |
| 10,730,879 B2 | 8/2020 | Carra et al. | |
| 2017/0260186 A1 | 9/2017 | Hu et al. | |
| 2020/0095249 A1 | 3/2020 | Kompella et al. | |

FOREIGN PATENT DOCUMENTS

| | | | |
|---|---|---|---|
| CN | 106279171 A | 1/2017 | |
| CN | 106565716 A | 4/2017 | |
| CN | 106632337 A | 5/2017 | |
| CN | 107573345 A | 1/2018 | |
| CN | 108218872 A | 6/2018 | |
| CN | 108329318 A | 7/2018 | |
| EP | 3048104 A1 | 7/2016 | |
| WO | 2015092810 A2 | 6/2015 | |
| WO | 2016026380 A1 | 2/2016 | |
| WO | 2016097314 A1 | 6/2016 | |
| WO | WO 2016157136 A1 * | 6/2016 | ........... C07D 473/34 |
| WO | 2016108206 A2 | 7/2016 | |
| WO | 2016147206 A1 | 9/2016 | |
| WO | 2016157136 A1 | 10/2016 | |
| WO | 2016188506 A1 | 12/2016 | |
| WO | 2017093773 A1 | 6/2017 | |
| WO | 2017130221 A1 | 8/2017 | |
| WO | 2017137097 A1 | 8/2017 | |
| WO | 2017175184 A1 | 10/2017 | |
| WO | 2017191608 A1 | 11/2017 | |

* cited by examiner

*Primary Examiner* — John M Mauro

(57) ABSTRACT

The invention relates to a crystalline pyridine or N,N-dimethylacetamide solvated solid-state form of idelalisib (IDB). The invention is also directed to the preparation of the aforesaid solvated solid-state forms of IDB. Furthermore, the invention is directed to the use of the aforesaid solvated solid-state forms of IDB.

19 Claims, 9 Drawing Sheets

PYRIDINE OR N,N-DIMETHYL ACETAMIDE SOLVATED SOLID STATE FORMS OF SOLVATED IDELALISIB, THEIR USE AND PREPARATION

CROSS-REFERENCE TO RELATED APPLICATIONS

This application is a continuation of International Application No. PCT/US2019/022757, filed Mar. 18, 2019, which claims priority to U.S. Provisional Patent Application No. 62/644,062, filed Mar. 16, 2018, the disclosures of which are incorporated herein by reference in their entireties for all purposes.

FIELD OF THE INVENTION

The invention relates to a crystalline pyridine or N,N-dimethyl acetamide (DMA) solvated solid-state form of idelalisib (IDB), the preparation of the aforesaid solvated forms and their use.

BACKGROUND OF THE INVENTION

IDB, (S)-2-(1-(9H-purin-6-ylamino)propyl)-5-fluoro-3-phenyl quinazolin-4(3H)-one, of the Formula I below, is an inhibitor of 25 phosphoinositide 3-kinase (PI3K) delta, a

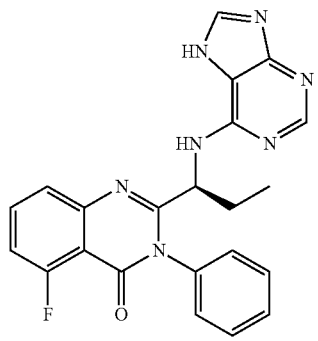

Formula I protein that is critical for the activation, proliferation and survival of B lymphocytes. PI3K delta signaling is hyperactive in many B-cell leukemias and lymphomas and drives proliferation, survival and trafficking to lymphoid tissue. IDB is approved by US FDA for treating relapsed chronic lymphocytic leukemia (CLL), relapsed follicular B-cell non-Hodgkin lymphoma (FL) and relapsed small lymphocytic lymphoma (SLL).

The preparation of IDB is disclosed in RE44638, but does not disclose the existence of any polymorphic form. U.S. Pat. Nos. 8,865,730, 9,469,643, 9,518,059 and 9,708,327, US Patent Application Nos. 20160376274, 20170260186 and 2018037584, PCT Patent Application Nos. WO2015092810, WO2016097314, WO2016147206, WO2016157136, WO2016188506, WO2017093773, WO2017137097 and WO2017175184 discloses solid-state forms of IDB. None of the references disclose a pyridine or DMA solvated form of IDB.

SUMMARY OF THE INVENTION

The invention relates to a crystalline pyridine or DMA solvated solid-state form of idelalisib (IDB). The invention is also directed to the preparation of the aforesaid solvated solid-state forms of IDB. Furthermore, the invention is directed to the use of the aforesaid solvated solid-state forms of IDB.

DETAILED DESCRIPTION OF THE INVENTION

Figure 1:
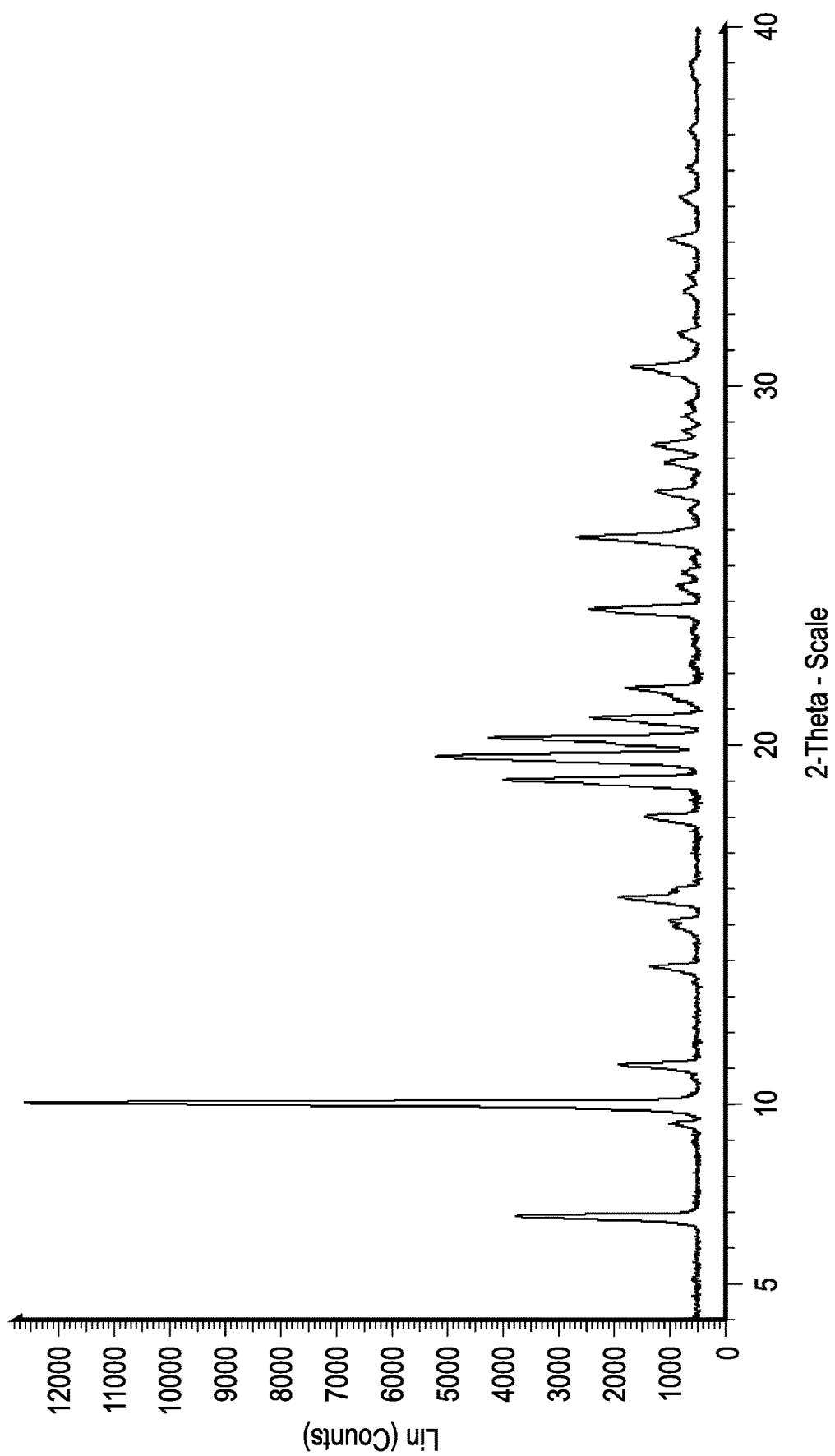
FIG. 1 is an XRPD pattern of crystalline pyridine solvated solid-state form of IDB.
Figure 2:
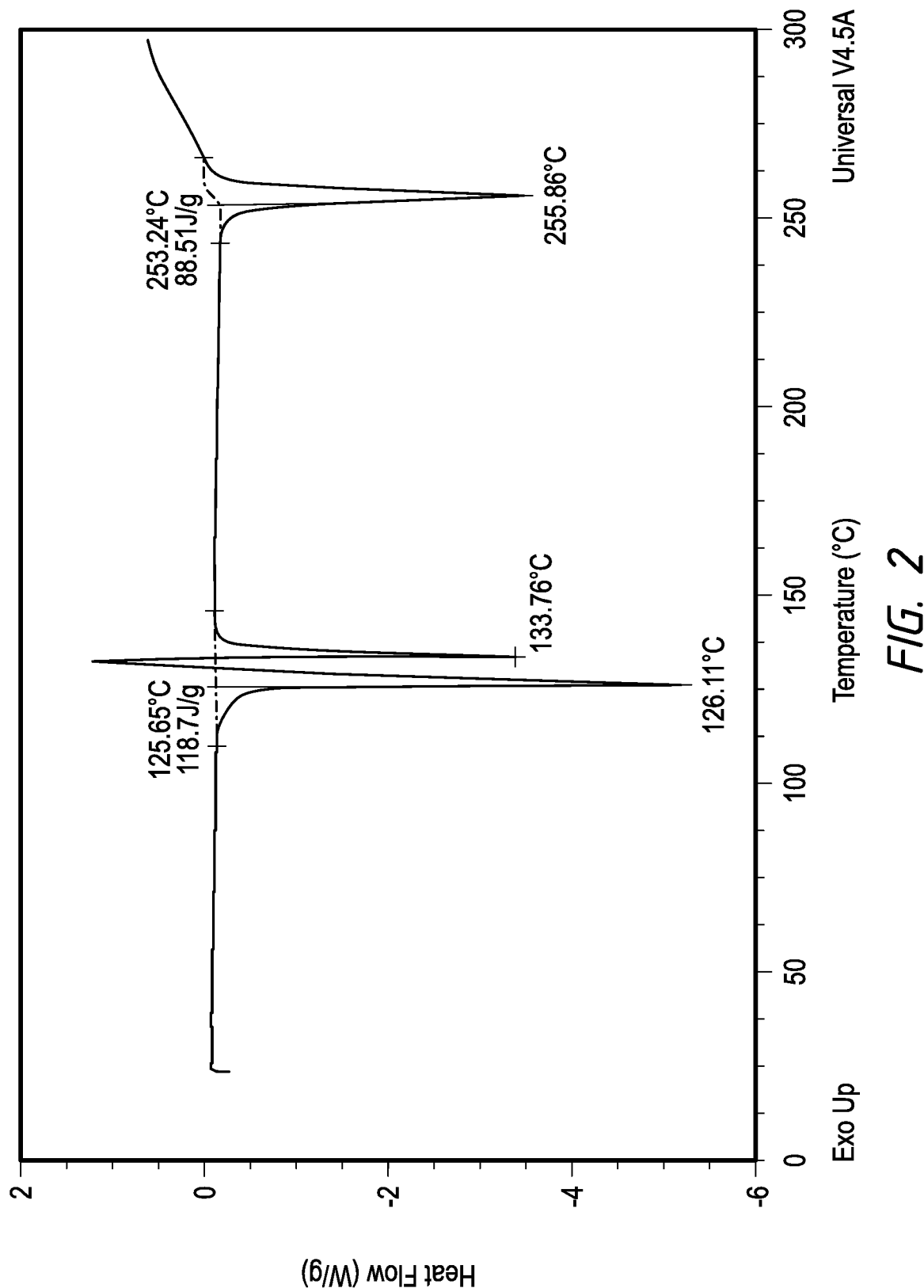
FIG. 2 is a DSC curve of crystalline pyridine solvated solid-state form of IDB.
Figure 3:
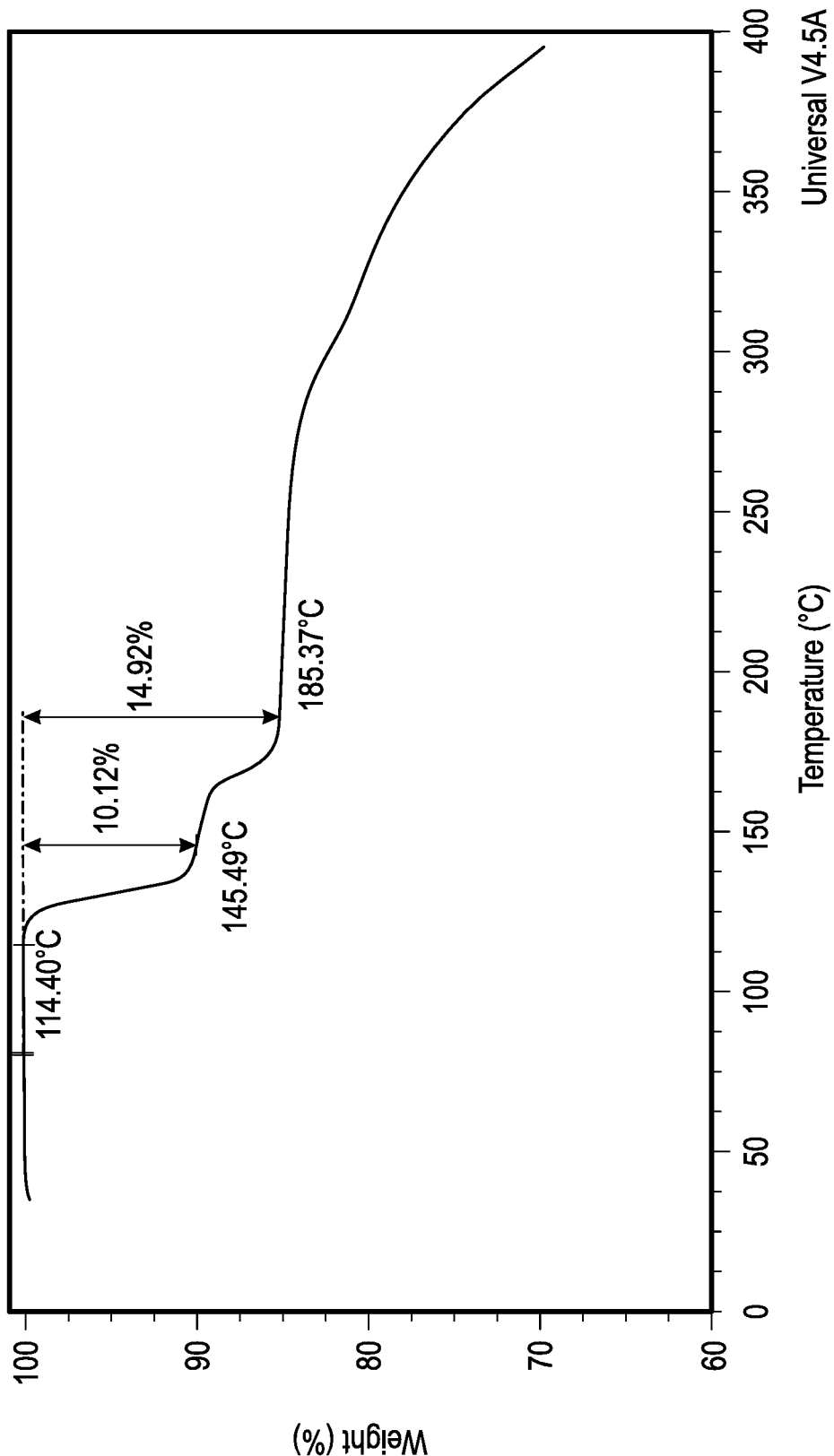
FIG. 3 is a TGA curve of crystalline pyridine solvated solid-state form of IDB.
Figure 4:
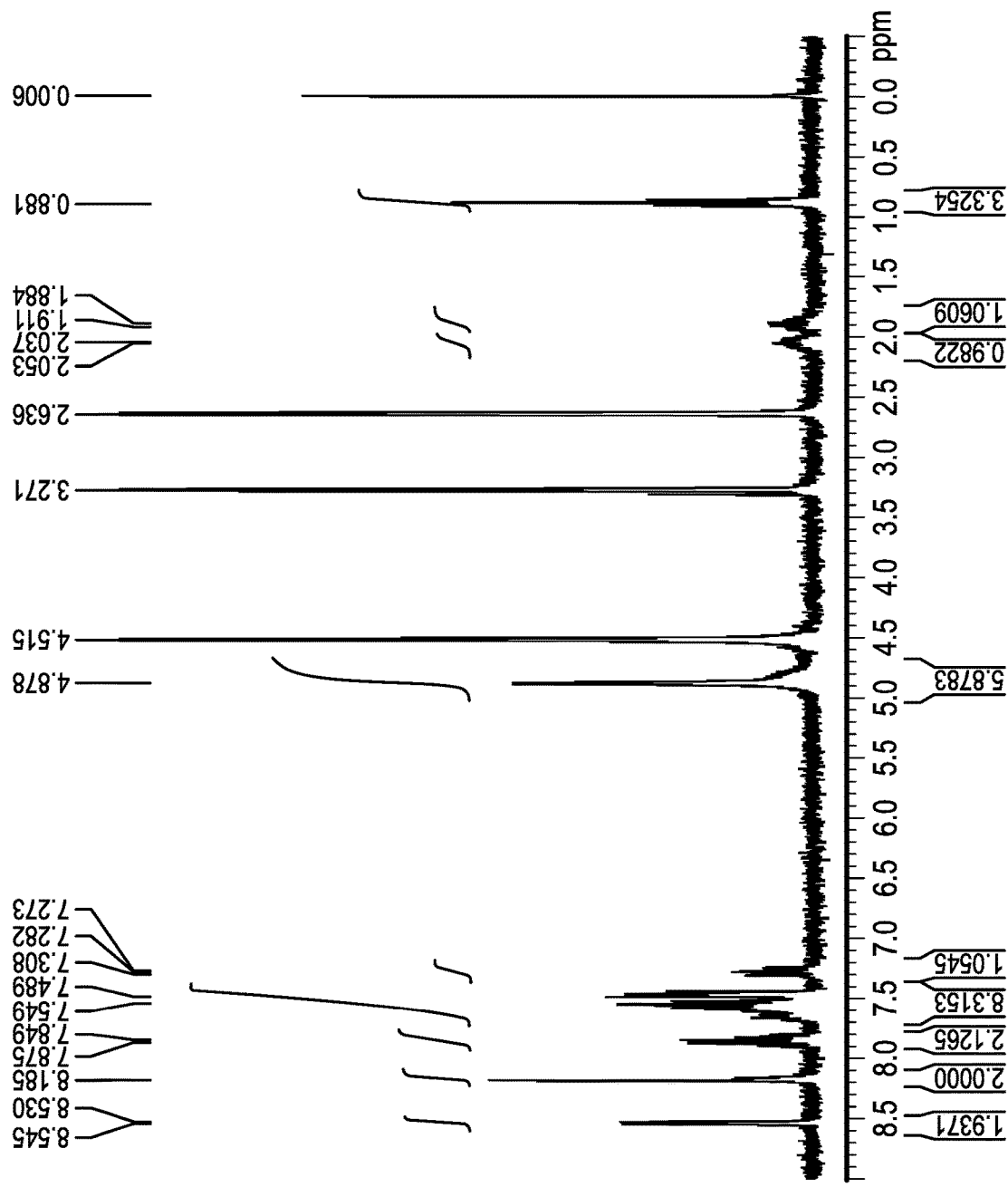
FIG. 4 is a $^1$H NMR spectra of crystalline pyridine solvated solid-state form of IDB.

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles described herein may be applied to other examples and applications without departing from the spirit and scope of the various embodiments. Therefore, the various embodiments are not intended to be limited to the examples described herein and shown, but are to be accorded the scope consistent with the claims.

The term "solid-state form" of IDB, as used herein, includes crystalline or polymorphic forms, amorphous phases, and solvates.

The use of the term "about" includes and describes the value or parameter per se. For example, "about x" includes and describes "x" per se. The term "about" when used in association with a measurement, or used to modify a value, a unit, a constant, or a range of values, refers to variations of +/−5 percent.

The term "substantially" or "substantially free/pure" with respect to a solid-state form means that the form contains about less than 30 percent, about less than 20 percent, about less than 15 percent, about less than 10 percent, about less than 5 percent, or about less than 1 percent by weight of impurities. Impurities may, for example, include other polymorphic forms, water and solvents other than that in the crystalline solid-state form.

The term "room temperature" is defined as a temperature between 15-29° C.; preferably between 20-23° C.

The term "to dry/drying/dried", as used in this patent application, means to dry/drying/dried at 45° C. and under vacuum.

All ranges recited herein include the endpoints. Terms such as "about," "generally," and "substantially," are to be construed as modifying a term or value such that it is not an absolute. This includes, at very least, the degree of expected experimental error, technique error and instrument error for a given technique used to measure a value.

The term "pharmaceutically acceptable" means that which is useful in preparing a pharmaceutical composition that is generally non-toxic and is not biologically undesirable, and includes that which is acceptable for veterinary use and/or human pharmaceutical use.

The term "pharmaceutical composition" is intended to encompass a drug product including the active ingredient(s), pharmaceutically acceptable excipients that make up the carrier, as well as any product which results, directly or indirectly, from combination, complexation or aggregation of any two or more of the ingredients. Accordingly, the pharmaceutical compositions encompass any composition made by admixing the active ingredient, active ingredient dispersion or composite, additional active ingredient(s), and pharmaceutically acceptable excipients.

EMBODIMENTS

It is therefore an object of the present invention to provide a pyridine or DMA solvated solid-state form of IDB that is purifiable, stable and scalable. It is also the object of the present invention to provide a pyridine or DMA solvated solid-state form of IDB that is capable of being isolated and handled. It is further an object of the present invention to provide a process for the preparation of such a pyridine or DMA solvated solid-state form of IDB; particularly wherein the IDB therein is purified. Another object of the invention is the use of a pyridine or DMA solvated solid-state form of IDB for preparing amorphous IDB. It is a yet another object of the invention to use of a pyridine or DMA solvated solid-state form of IDB to prepare a pharmaceutical dosage form of IDB.

In another general aspect, there is provided a process for the preparation of solid-state pyridine solvate form of IDB, comprising:
(a) dissolving IDB in pyridine to form a pyridine solution of IDB; and
(b) evaporating slowly the pyridine solution of IDB to yield the solid-state pyridine solvate form of IDB.

In another general aspect, there is provided a process for the preparation of solid-state pyridine solvate form of IDB, comprising:
(a) dissolving IDB in pyridine at 50-60° C. to form a pyridine solution of IDB; and
(b) cooling the solution to yield the solid-state pyridine solvate form of IDB.

In one embodiment, the dissolving is conducted at about 60° C. In one embodiment, the cooling is conducted at about −10° C.

In another general aspect, there is provided a process for the preparation of solid-state DMA solvate form of IDB, comprising:
(a) dissolving IDB in DMA to form a DMA solution of IDB; and
(b) evaporating slowly DMA to yield the solid-state DMA solvate form of IDB.

In another general aspect, there is provided a process for the preparation of solid-state DMA solvate form of IDB, comprising:
(a) dissolving IDB in DMA to form a DMA solution of IDB;
(b) adding water to the DMA solution of IDB; and (c) stirring the DMA solution of IDB with added water with cooling to about 5° C. to yield the solid-state DMA solvate form of IDB.

In another general aspect, there is provided a process for the preparation of solid-state amorphous form of IDB, comprising:
(a) adding water to a 0.4M DMA solution of IDB in a 3:1 v:v (volume:volume) respectively; and
(b) vacuum filtering the resultant mixture of step (a) to yield solid-state amorphous form of IDB.

The aforesaid process for preparing amorphous IDB, further comprising steps
(c) rinsing the solid-state amorphous form of IDB with water;
(d) rinsing the solid-state amorphous form of IDB with methanol at about 0° C.; and
(e) drying the solid-state amorphous form of IDB under vacuum.

The aforesaid process wherein the drying is conducted at about 25° C.

In another general aspect, there is provided an amorphous solid dispersion comprising IDB and one or more pharmaceutically acceptable excipients.

In another general aspect, there is provided a pharmaceutical composition comprising an amorphous IDB together with one or more pharmaceutically acceptable carriers, excipients or diluents.

In another general aspect, there is provided a pharmaceutical composition comprising an amorphous solid dispersion comprising IDB together with one or more of pharmaceutically acceptable carriers, excipients or diluents.

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles described herein may be applied to other examples and applications without departing from the spirit and scope of the various embodiments. Therefore, the various embodiments are illustrative of the present invention and the invention is not intended to be limited to the examples described herein and shown.

Example

Analytical Experimental
XRPD (X-Ray Powder Diffractometry)
Diffractograms are obtained with laboratory diffractometer, BRUKER D-8 Discover diffractometer, using radiation CuKa (X=1.542 A).

Relative intensities for peak values can vary depending on several factors, including sample preparation, mounting, and analytical procedure and settings of the instrument that is used to obtain the spectrum.

DSC (Differential Scanning Calorimetry)
Polymorph Solid-State Form:
DSC measurements are performed on a calorimeter, TA Instruments Q2000.

The samples are weighed in aluminum pans/crucibles covered by lids. Investigations were performed in a temperature range of 20-350° C. with a heating rate of 10° C./min, purging with nitrogen at a flow rate of 50 mL/min.
Amorphous Solid-State Form:
DSC measurements are performed on a calorimeter, TA Instruments Q2000.

The samples are weighed in aluminum pans/crucibles covered by lids with pin holes. Investigations are performed in a temperature range of 0-200° C. with a heating rate of 1.5° C./min (Amplitude=0.5° C. and Period=60 s), purging with nitrogen at a flow rate of 50 mL/min.

Analysis—TGA (ThermoGravimetric Analysis)

TGA measurements are recorded using TA Q5000 instrument. The samples are weighed in aluminum pans. TGA investigations are performed at a heating rate of 10.0° C./min over a temperature range of 20° C.-400° C., purging with nitrogen at a flow rate of 25 mL/min.

Analysis—$^1$H NMR $^1$H NMR measurements are recorded using Bruker 300 MHz Avance NMR spectrometer in DMSO-d6.

I. Solid-State Form I of Pyridine Solvate of IDB

Single crystals of the solid-state form of the pyridine solvate of IDB are made by dissolving IDB in pyridine and allowing the solvent to slowly evaporate. Clear, colorless crystals are isolated.

The solid-state form of the pyridine solvate of IDB is also made by dissolving IDB in warm (about 60° C.) pyridine, cooling to about −10° C., stirring for about 24 hours, and vacuum filtering the resulting white powder. The powder is then dried under reduced pressure, e.g., a vacuum oven, at about 45° C. for 24 hours.

The XRPD of the solid-state pyridine solvate of IDB can be distinguished by 3 or more peaks at 6.82, 9.977, 18.993, 19.643, 20.16, or 20.719 2Θ. FIG. 1 is an XRPD pattern of crystalline pyridine solvated solid-state form of the pyridine solvate of IDB, and 2Θ, d-spacing and relative % intensity values for peaks are shown in Table I.

TABLE I

| Angle 2Θ | d value Angstrom | Intensity % % |
|---|---|---|
| 6.82 | 12.94977 | 30.4 |
| 9.98 | 8.85879 | 100 |
| 11.04 | 8.00778 | 15.2 |
| 15.69 | 5.64273 | 15.3 |
| 17.97 | 4.93373 | 11.6 |
| 18.99 | 4.66894 | 32.3 |
| 19.64 | 4.51571 | 40.8 |
| 20.16 | 4.40109 | 33.5 |
| 20.72 | 4.28374 | 19.5 |
| 21.53 | 4.12325 | 13.3 |
| 23.74 | 3.74423 | 19.2 |
| 25.76 | 3.45529 | 21.2 |
| 30.51 | 2.92729 | 13.2 |

The angle measurements are ±0.2° 2Θ.

The XRPD, DSC, TGA, and $^1$H NMR (See respectively FIGS. 1-4) are directed to the solid-state form of the pyridine solvate of IDB.

Single crystal parameters for the solid-state form of the pyridine solvate of IDB as determined by SCXRD are:
a=7.5375(2)
b=17.3362(4)
c=18.4048(4)
α=90°
β=90°
γ=90°

Figure 5:
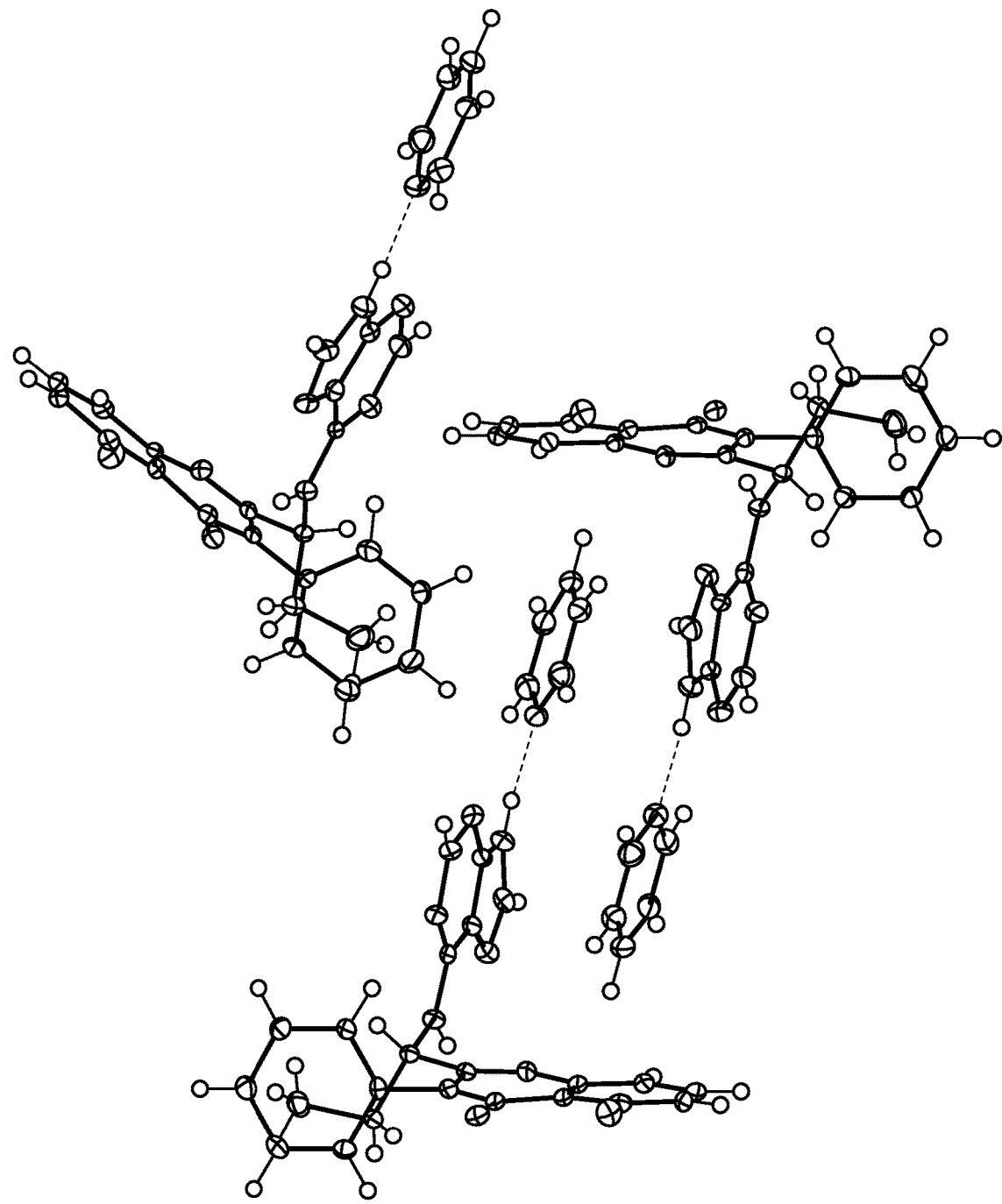
FIG. 5 is a three-dimensional structure of crystalline pyridine solvated solid-state form of IDB that is discerned from SCXRD.

FIG. 5 shows a three-dimensional structure of crystalline pyridine solvated solid-state form of IDB that is discerned from SCXRD. The $^1$H NMR, TGA and single crystal results indicate a 1:1 pyridine:IDB solvate, with pyridine comprising 16% of the mass of the crystalline material.

II. Solid-State Form I of DMA Solvate of IDB

Single crystals of the solid-state form of the DMA solvate are grown by dissolving IDB in DMA and allowing the solvent to slowly evaporate, to produce clear, colorless rods.

The solid-state form of the DMA solvate of IDB is also made by dissolving IDB in DMA and adding water as an antisolvent and then stirring for about 24 hours at about −10° C. The resulting powder is vacuum filtered and dried in a vacuum oven for about 24 hours at about 45° C.

Figure 6:
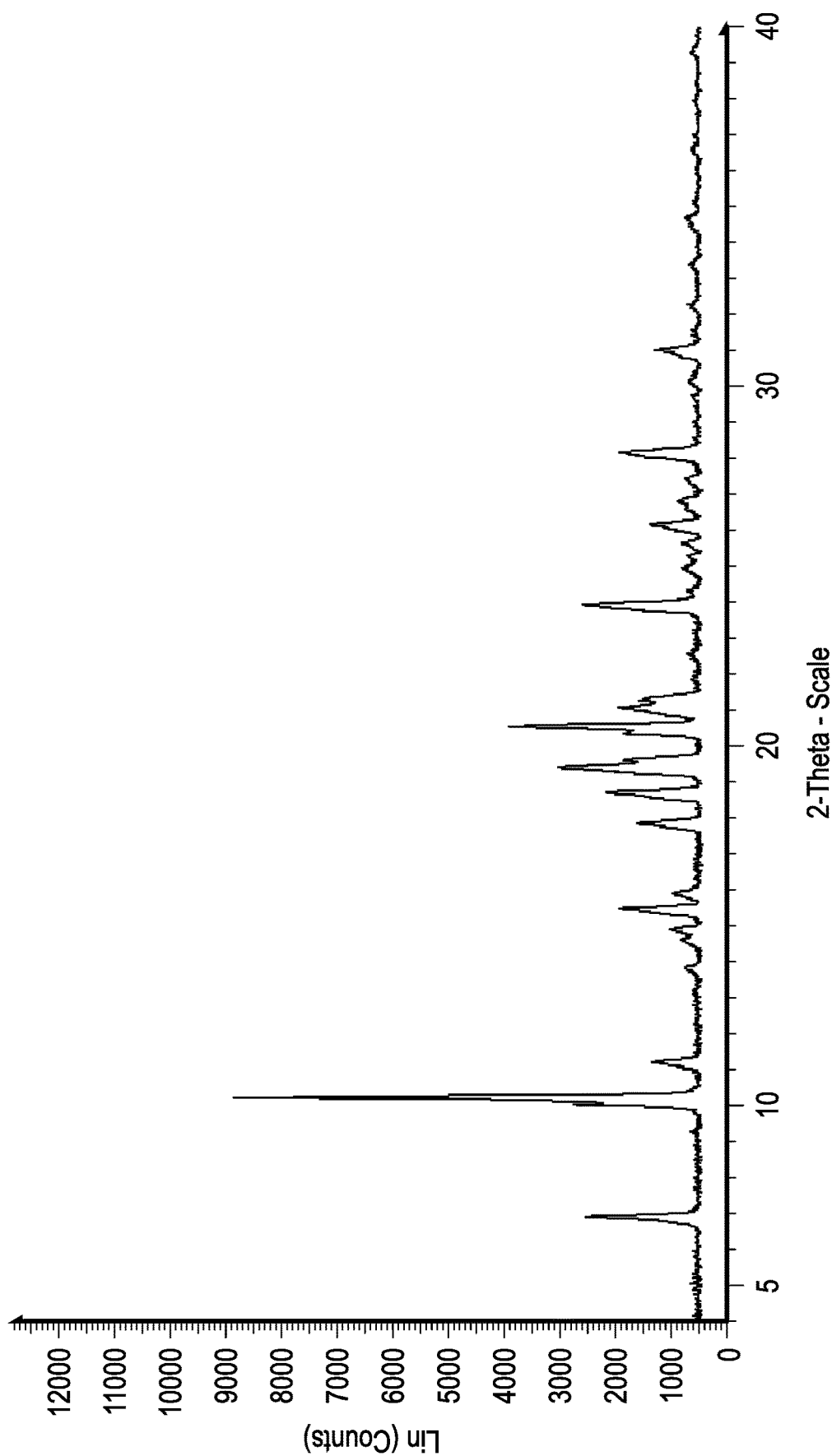
FIG. 6 is an XRPD pattern of crystalline DMA solvated solid-state form of IDB.

The solid-state form of the DMA solvate of IDB is distinguished by a peak at 6.88 or 10.20 and a pair of peaks at either 19.39 and 19.60, 20.35 and 20.53, or 21.04 and 21.28° 2Θ. FIG. 6 is an XRPD pattern of crystalline DMA solvated solid-state form of the DMA solvate of IDB, and 2Θ, d-spacing and relative % intensity values for peaks are shown in Table II.

TABLE II

| Angle 2Θ | d value Angstrom | Intensity % % |
|---|---|---|
| 6.88 | 12.83604 | 24.4 |
| 10.20 | 8.66553 | 100 |
| 11.20 | 7.89561 | 10.3 |
| 14.58 | 6.06906 | 3.7 |
| 14.87 | 5.95285 | 6.3 |
| 15.45 | 5.73234 | 17.5 |
| 15.87 | 5.57905 | 6.3 |
| 17.83 | 4.97132 | 14.7 |
| 18.69 | 4.7447 | 22.1 |
| 19.39 | 4.57501 | 32.7 |
| 19.60 | 4.52572 | 18.5 |
| 20.35 | 4.3605 | 18.5 |
| 20.53 | 4.32251 | 43.2 |
| 21.04 | 4.21975 | 19.6 |
| 21.28 | 4.17143 | 13.3 |
| 23.90 | 3.71975 | 24.9 |
| 24.93 | 3.5694 | 3.8 |
| 25.62 | 3.47421 | 3.8 |
| 26.14 | 3.40674 | 10.2 |
| 26.81 | 3.3231 | 4.4 |
| 28.13 | 3.16992 | 16.7 |
| 31.00 | 2.88219 | 9.4 |

The angle measurements are ±0.2° 2Θ.

Figure 7:
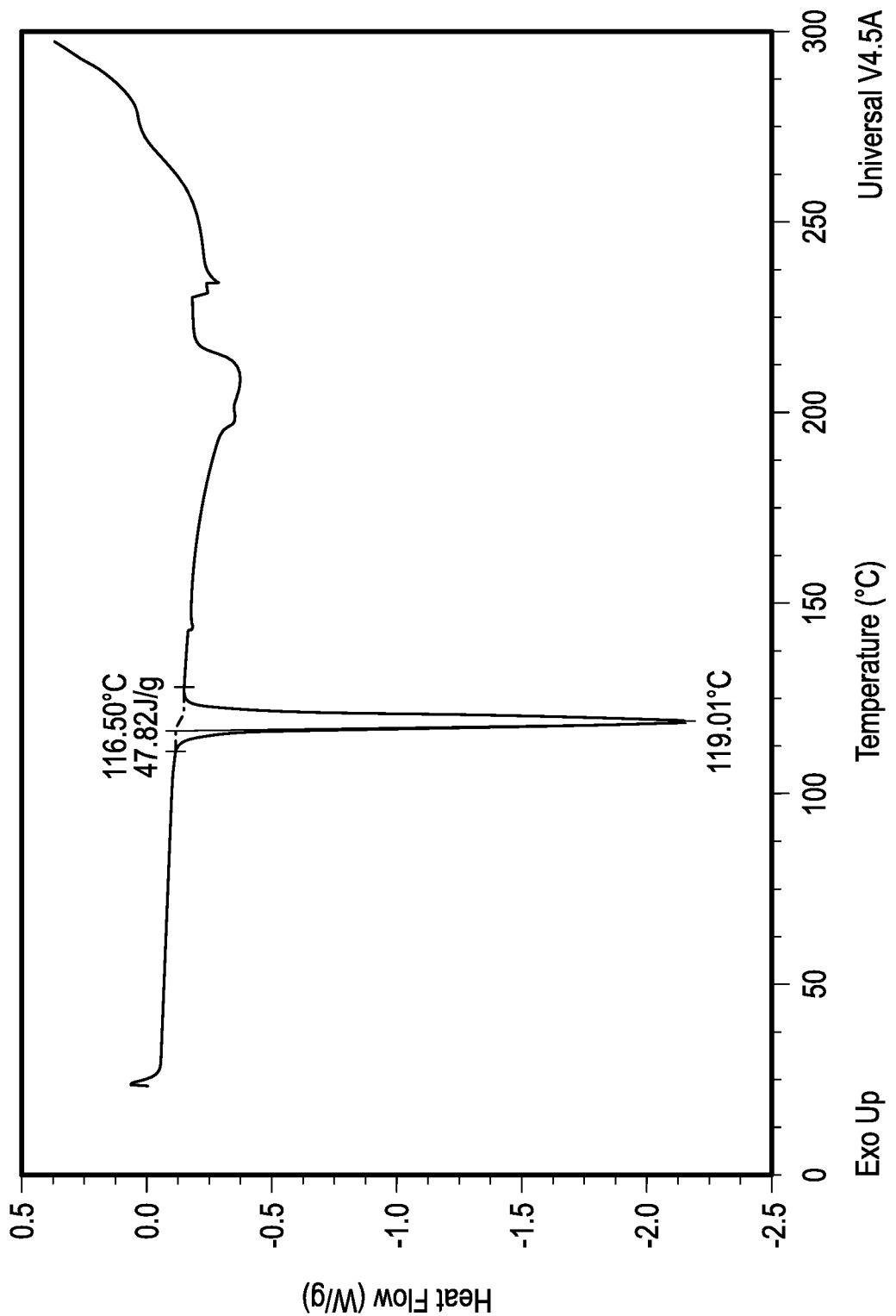
FIG. 7 is a DSC curve of crystalline DMA solvated solid-state form of IDB.
Figure 8:
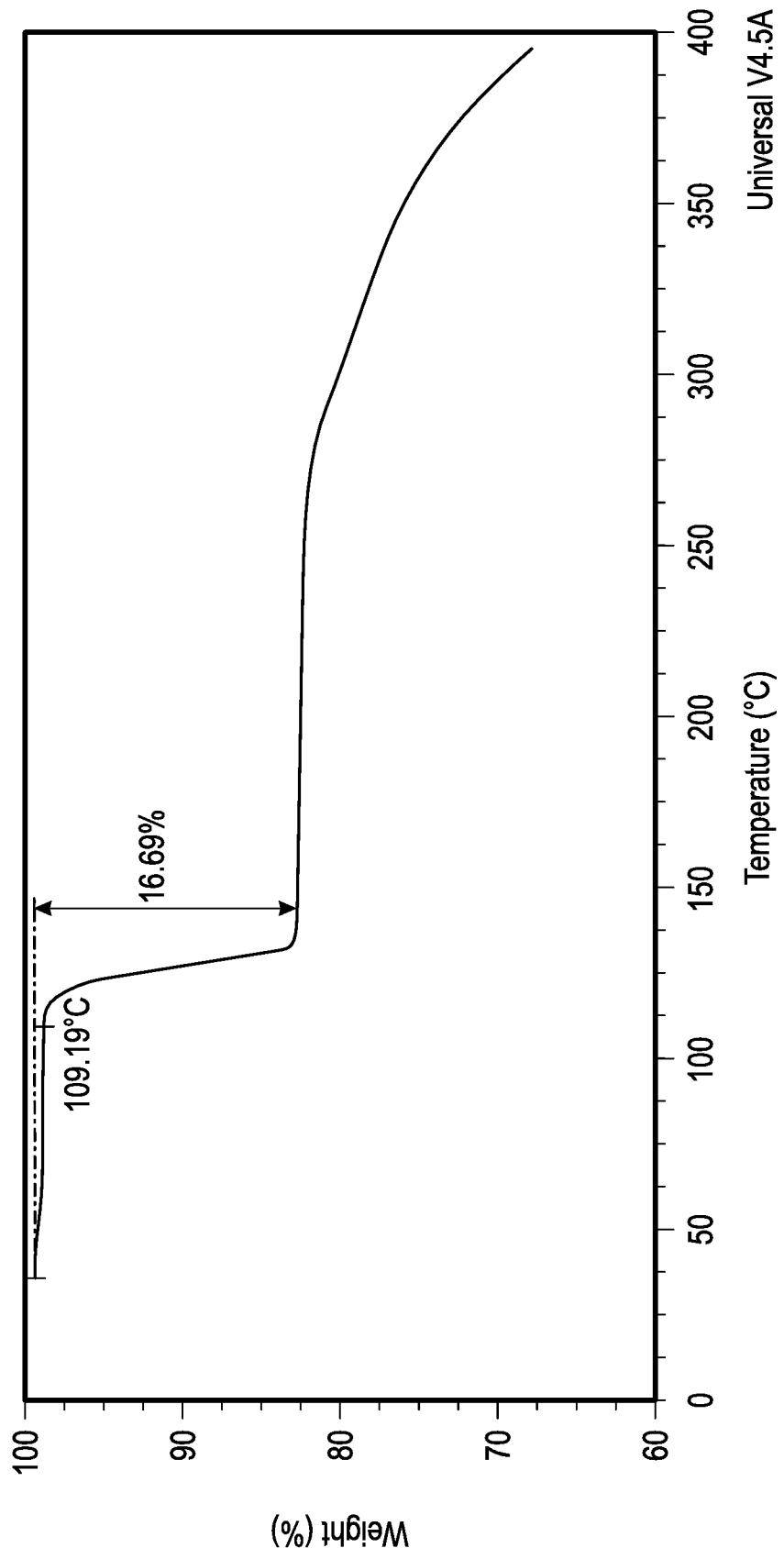
FIG. 8 is a TGA curve of crystalline DMA solvated solid-state form of IDB.

The XRPD, DSC, and TGA (See respectively FIGS. 6-8) are directed to the solid-state form of the DMA solvate of IDB.

Single crystal parameters for the solid-state form of the DMA solvate of IDB as determined by SCXRD are:
a=7.7950(2)
b=16.9767(4)
c=18.8133(4)
α=90°
β=90°
γ=90°

Figure 9:
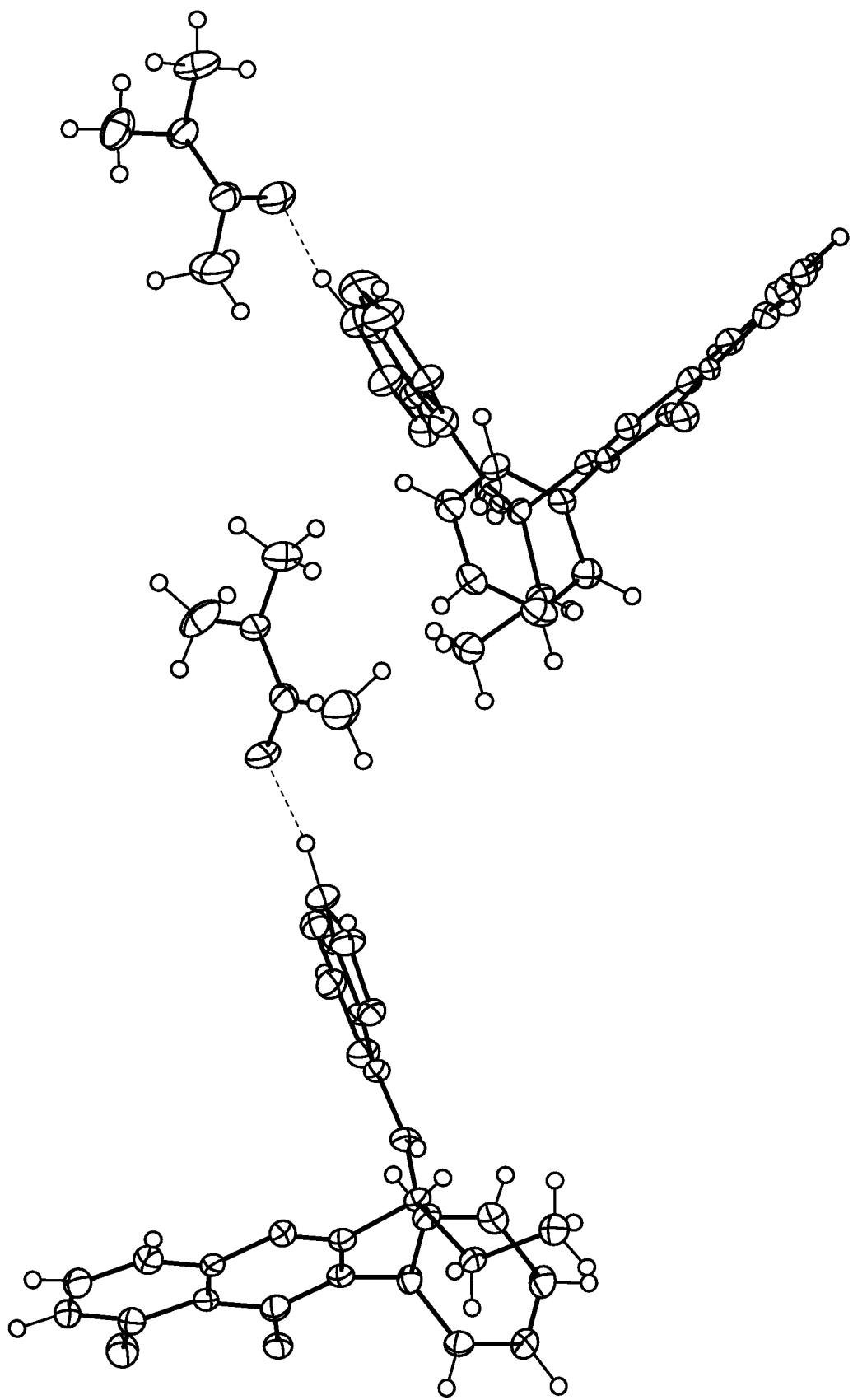
FIG. 9 is a three-dimensional structure of crystalline DMA solvated solid-state form of IDB that is discerned from SCXRD.

FIG. 9 shows a three-dimensional structure of crystalline DMA solvated solid-state form of IDB that is discerned from SCXRD. The TGA and single crystal results indicate a 1:1 DMA:IDB solvate.

III. Solid-State Amorphous Form of IDB 1.03 g of DMA solvate of IDB is dissolved in 5 mL of DMA and stirred until it became a clear, yellow solution. Solution is then added to 15 mL of water by pipette over the course of one minute. The resulted solution is stirred and vacuum filtered for 20 minutes, followed by a first rinse with 1 mL of water, and then a second rinse with 3 mL of MeOH at 0. The material is then dried in a vacuum oven at 25° C. for 2 days. Material is tested by XRPD, DVS, DSC, TGA, KF, and $^1$H NMR. Material is amorphous and does not revert to a crystalline form over 7 days at 40° C. and 75% humidity.

IV. Formulation of Solid-State Amorphous Form of IDB

Dispersion formulation of IDB: 18 mg of amorphous IDB is dry ground with 90 mg of sucrose for 6 hours at 250 RPM in the Fritsch Laboratory Planetary Laboratory Planetary Mono Mill Pulverisette system. The product is exposed to 75% humidity at 40° C. for 3 weeks with no reversion to crystalline form.

The above description is presented to enable a person of ordinary skill in the art to make and use the various embodiments. Descriptions of specific devices, techniques, and applications are provided only as examples. Various modifications to the examples described will be readily apparent to those of ordinary skill in the art, and the general principles described herein—above and after, may be applied to other examples and applications without departing from the scope of the present invention. Thus, the various embodiments are not intended to be limited to the examples described.

While the present invention has been described in terms of its specific embodiments, certain modifications and equivalents will be apparent to those skilled in the art and are intended to be included within the scope of the present invention.

The invention claimed is:

1. A compound which is a crystalline pyridine or N,N-dimethyl acetamide solvate of idelalisib.

2. The compound of claim 1 which is the pyridine solvate of idelalisib.

3. The compound of claim 1 which is the N,N-dimethylacetamide solvate of idelalisib.

4. The compound of claim 2 having at least 3 or more X-ray powder diffraction peaks selected from about 6.82, 9.98, 18.99, 19.64, 20.16, and 20.72 2Θ measured by CuKa radiation.

5. The compound of claim 3 having one or two X-ray powder diffraction peaks selected from about 6.88 or 10.20 2Θ measured by CuKa radiation.

6. The compound of claim 5 further comprising at least one pair of X-ray powder diffraction peaks at either about 19.39 and 19.60, 20.35 and 20.53, or 21.04 and 21.28° 2Θ measured by CuKa radiation.

7. The compound of claim 2 having one to three DSC peaks at 126.1° C., 133.8° C. and 255.9° C.

8. The compound of claim 3 having a DSC peak at 119.0° C.

9. The compound of claim 2 having a thermal gravimetric curve having about a 10.1% weight loss in the range of about 114.4° C. to 145.5° C.

10. The compound of claim 2 having a thermal gravimetric curve having about a 4.8% weight loss in the range of about 145.5° C. to about 185.4° C.

11. The compound of claim 3 having a thermal gravimetric curve having about a 16.7% weight loss in the range of about 109.1° C. to 120.5° C.

12. A process for the preparation of solid-state pyridine solvate form of idelalisib, comprising:
    (a) dissolving idelalisib in pyridine to form a pyridine solution of idelalisib; and
    (b) evaporating slowly the pyridine solution of idelalisib to yield the solid-state pyridine solvate form of idelalisib.

13. A process for the preparation of solid-state pyridine solvate form of idelalisib, comprising:
    (a) dissolving idelalisib in pyridine at about 50-60° C. to form a pyridine solution of idelalisib; and
    (b) cooling the solution to yield the solid-state pyridine solvate form of idelalisib.

14. The process of claim 13 wherein the dissolving is conducted at about 60° C.

15. The process of claim 13 wherein the cooling is conducted to about −10° C.

16. A process for the preparation of solid-state N,N-dimethylacetamide solvate form of idelalisib, comprising:
    (a) dissolving idelalisib in N,N-dimethylacetamide to form a N,N-dimethylacetamide solution of idelalisib; and
    (b) evaporating N,N-dimethylacetamide to yield the solid-state N,N-dimethylacetamide solvate form of idelalisib.

17. A process for the preparation of solid-state N,N-dimethylacetamide solvate form of idelalisib, comprising:
    (a) dissolving idelalisib in N,N-dimethylacetamide to form a N,N-dimethylacetamide solution of idelalisib;
    (b) adding water to the N,N-dimethylacetamide solution of idelalisib; and
    (c) stirring the N,N-dimethylacetamide solution of idelalisib with added water with cooling to about 5° C. to yield the solid-state N,N-dimethylacetamide solvate form of idelalisib.

18. A process for the preparation of solid-state amorphous form of idelalisib, comprising:
    (a) adding water to a 0.4M N,N-dimethylacetamide solution of idelalisib in a 3:1 v:v respectively;
    (b) vacuum filtering the resultant mixture of step (a) to yield solid-state amorphous form of idelalisib;
    (c) rinsing the solid-state amorphous form of idelalisib with water;
    (d) rinsing the solid-state amorphous form of idelalisib with methanol at about 0° C.; and
    (e) drying the solid-state amorphous form of idelalisib under vacuum.

19. The process of claim 18 wherein the drying is conducted at about 25° C.

* * * * *